United States Patent
Pandharipande et al.

(10) Patent No.: US 8,694,274 B2
(45) Date of Patent: Apr. 8, 2014

(54) DISTRIBUTED SPECTRUM SENSING

(75) Inventors: Ashish Vijay Pandharipande, Eindhoven (NL); Hongming Yang, Eindhoven (NL); Johan Paul Marie Gerard Linnartz, Eindhoven (NL)

(73) Assignees: Koninklijke Philips N.V., Eindhoven (NL); NXP Semiconductor Netherlands B.V., Eindhoven (NL)

( * ) Notice: Subject to any disclaimer, the term of this patent is extended or adjusted under 35 U.S.C. 154(b) by 269 days.

(21) Appl. No.: 12/922,697

(22) PCT Filed: Mar. 12, 2009

(86) PCT No.: PCT/IB2009/051036
§ 371 (c)(1),
(2), (4) Date: Sep. 15, 2010

(87) PCT Pub. No.: WO2009/115957
PCT Pub. Date: Sep. 24, 2009

(65) Prior Publication Data
US 2011/0022342 A1    Jan. 27, 2011

(30) Foreign Application Priority Data
Mar. 18, 2008  (EP) .................................... 08152863

(51) Int. Cl.
G06F 19/00   (2011.01)
G06F 17/18   (2006.01)

(52) U.S. Cl.
USPC ............................................ 702/75; 702/181

(58) Field of Classification Search
USPC ....................................... 702/75, 181; 455/68
See application file for complete search history.

(56) References Cited

U.S. PATENT DOCUMENTS

| 6,909,997 B2 | 6/2005 | Chen et al. |
| 7,378,953 B2 * | 5/2008 | Coronel et al. ............ 340/539.1 |
| 2006/0087423 A1 | 4/2006 | Coronel et al. |

FOREIGN PATENT DOCUMENTS

CN    1838572 A    9/2006

OTHER PUBLICATIONS

Ghasemi et al: "Impact of User Collaboration on the Performance of Sensing-Based Opportunistic Spectrum Access"; IEEE Vehicular Technology Conference, Sep. 2006 (IEEE VTC Fall), pp. 1-6.
Ghasemi et al: "Opportunistic Spectrum Access in Fading Channels Through Collaborative Sensing"; Journal of Communications, vol. 2, No. 2, Mar. 2007, pp. 71-82.
Zhen et al: "IEEE Body Area Networks for Medical Applications"; 4th International Symposium on Wireless Communication Systems (IEEE ISWCS), 2007, pp. 327-331.
Visotsky et al: "On Collaborative Detection of TV Transmissions in Support of Dynamic Spectrum Sharing"; IEEE Symposium on New Frontiers in Dynamic Spectrum Access Networks, Nov. 2005, pp. 338-345.
Yu et al: "A Paradigm for Distributed Detection Under Communication Constraints"; Proceedings of International Symposium on Information Theory, Sep. 1995, p. 293.

* cited by examiner

*Primary Examiner* — Bryan Bui

(57) ABSTRACT

In summary, the invention relates to a device, a system, a method and a computer program for spectrum sensing. A detection procedure for detecting a signal of interest or an event by using a plurality of sensing devices capable of communicating with a central unit is proposed. The sensing devices can compute soft detection metrics and communicate this information to a central unit, where the information may be used to make a final detection decision using a certain specified rule. The signaling overhead of the proposed approach can be of the same order as that of a hard signaling approach. However, the proposed approach may achieve a better detection performance.

13 Claims, 5 Drawing Sheets

DISTRIBUTED SPECTRUM SENSING

FIELD OF THE INVENTION

The present invention generally relates to a device, a system, a method and a computer program for detecting a signal of interest in a certain frequency band or another kind of event.

BACKGROUND OF THE INVENTION

Current spectrum allocation models result in under-utilization of licensed (primary) spectrum over space and time, as is the case e.g. in VHF-UHF bands. This has led to a growing interest in flexible spectrum usage models. One such model provides a secondary usage of a spectrum that has been licensed for a primary wireless system. The secondary usage is enabled by a secondary cognitive wireless system. The operation of the secondary cognitive wireless system should not cause a harmful interference to primary system users. This requirement can be met if the secondary cognitive wireless system operates on portions of the spectrum that are not used for primary user transmissions. To determine these portions, the spectrum is monitored for primary user activity. This is done by spectrum sensing.

An energy detection may be used to determine by means of a single sensing unit whether or not a signal of known bandwidth is present in a given spectrum region of interest. More advanced detection techniques that exploit signal features and higher-order statistical properties have also been considered. In a cognitive wireless system, a number of such sensing units are available, and a detection performance can be improved by combining information from multiple sensing units.

Two approaches for combining information from multiple sensing units have been proposed up to now. On the one hand, each sensing unit can make a hard detection decision and transmit a binary result (1/0) thereof to a central unit, where the received bits are combined. A commonly used rule for combining the bits is a majority rule, where a final decision of signal present is made if a majority of received bits are 1s. The advantage of this approach is that the amount of signaling is low. However, making a hard detection decision results in a loss of implicit signal information, which cannot be exploited further at the central unit. This in turn impacts the final detection performance.

On the other hand, each sensing unit may simply transmit raw observations or some other form of the observations to a central unit. While this approach can result in a better detection performance, the amount of signaling involved therewith is unacceptably large.

A. Ghasemi and E. S. Sousa, "Impact of user collaboration on the performance of sensing-based opportunistic spectrum access", IEEE VTC Fall, pp. 1-6, September 2006, discloses that either energy values or 1-bit hard decisions are transmitted from individual sensors to a central fusion unit and are combined there to effect a spectrum sensing.

SUMMARY OF THE INVENTION

It is an object of the present invention to alleviate at least some of the above-described problems.

Accordingly, in a first aspect of the present invention a device is presented. The device comprises a sensing unit configured to sense a signal, a first computing unit configured to compute a value based on multiple samples of the sensed signal or a signal component derived therefrom, a second computing unit configured to compute a metric based on the value computed by the first computing unit, and a communicating unit configured to communicate the metric computed by the second computing unit. The device can be used to detect certain signals of interest in cognitive wireless systems and other systems or certain events in sensor networks and other networks. It may enable a better detection performance than previously proposed devices while not requiring much more signaling overhead.

In a second aspect of the present invention the first computing unit is configured to compute the value based on a sum of squared samples of the sensed signal or signal component. The second aspect can be combined with the first aspect.

In a third aspect of the present invention the second computing unit is configured to compute the metric based on conditional probabilities of the value. The third aspect can be combined with the first or second aspect.

In a fourth aspect of the present invention the metric is a function depending on conditional probabilities of the value related to different hypotheses. The fourth aspect can be combined with any one of the preceding aspects.

In a fifth aspect of the present invention the metric is a log-likelihood ratio or likelihood ratio. The fifth aspect can be combined with any one of the preceding aspects.

In a sixth aspect of the present invention the sensing unit is configured to collect samples of the sensed signal or signal component over an observation time. The sixth aspect can be combined with any one of the preceding aspects.

In a seventh aspect of the present invention the sensing unit is configured to sense a radio signal or physiological signal. The seventh aspect can be combined with any one of the preceding aspects.

In an eighth aspect of the present invention a system is presented. The system comprises a plurality of devices according to any one of the preceding aspects, and a central unit configured to receive metrics communicated by the devices, to combine the metrics and to decide based on the combined metrics which one of a plurality of hypotheses is true. The system can be utilized to detect certain signals of interest in cognitive wireless networks or certain events in sensor networks. It may provide a better detection performance than previously proposed systems, without requiring much more signaling overhead.

In a ninth aspect of the present invention the central unit is configured to combine the metrics by summing or multiplying them. The ninth aspect can be combined with the eighth aspect.

In a tenth aspect of the present invention the central unit is configured to make the decision by means of a threshold rule. The tenth aspect can be combined with the eighth or ninth aspect.

In an eleventh aspect of the present invention the plurality of devices are part of a cognitive wireless network or sensor network. The eleventh aspect can be combined with any one of the eighth to tenth aspects.

In a twelfth aspect of the present invention the system is configured to determine whether or not a signal of interest is present in a certain frequency band or to detect a certain event. The twelfth aspect can be combined with any one of the eighth to eleventh aspects.

In a thirteenth aspect of the present invention a method is presented. The method comprises sensing a signal, computing a value based on multiple samples of the sensed signal or a signal component derived therefrom, computing a metric based on the value computed in the first computing step, and communicating the metric computed in the second computing step.

In a fourteenth aspect of the present invention the method further comprises receiving metrics from a plurality of devices, combining the metrics, and deciding based on the combined metrics which one of a plurality of hypotheses is true. The fourteenth aspect can be combined with the thirteenth aspect.

In a fifteenth aspect of the present invention a computer program is presented. The computer program comprises program code means for causing a computer to carry out the steps of a method according to the thirteenth or fourteenth aspect when the computer program is carried out on a computer.

The proposed method and computer program can be used to detect certain signals of interest in cognitive wireless systems and other systems or certain events in sensor networks and other networks. They may enable a better detection performance than previously proposed methods and computer programs while not requiring much more signaling overhead.

Further advantageous modifications are defined in the dependent claims.

BRIEF DESCRIPTION OF THE DRAWINGS

These and other aspects of the present invention will be apparent from and elucidated by embodiments described hereinafter with reference to the accompanying drawings, in which.

DETAILED DESCRIPTION OF EMBODIMENTS

Figure 1:
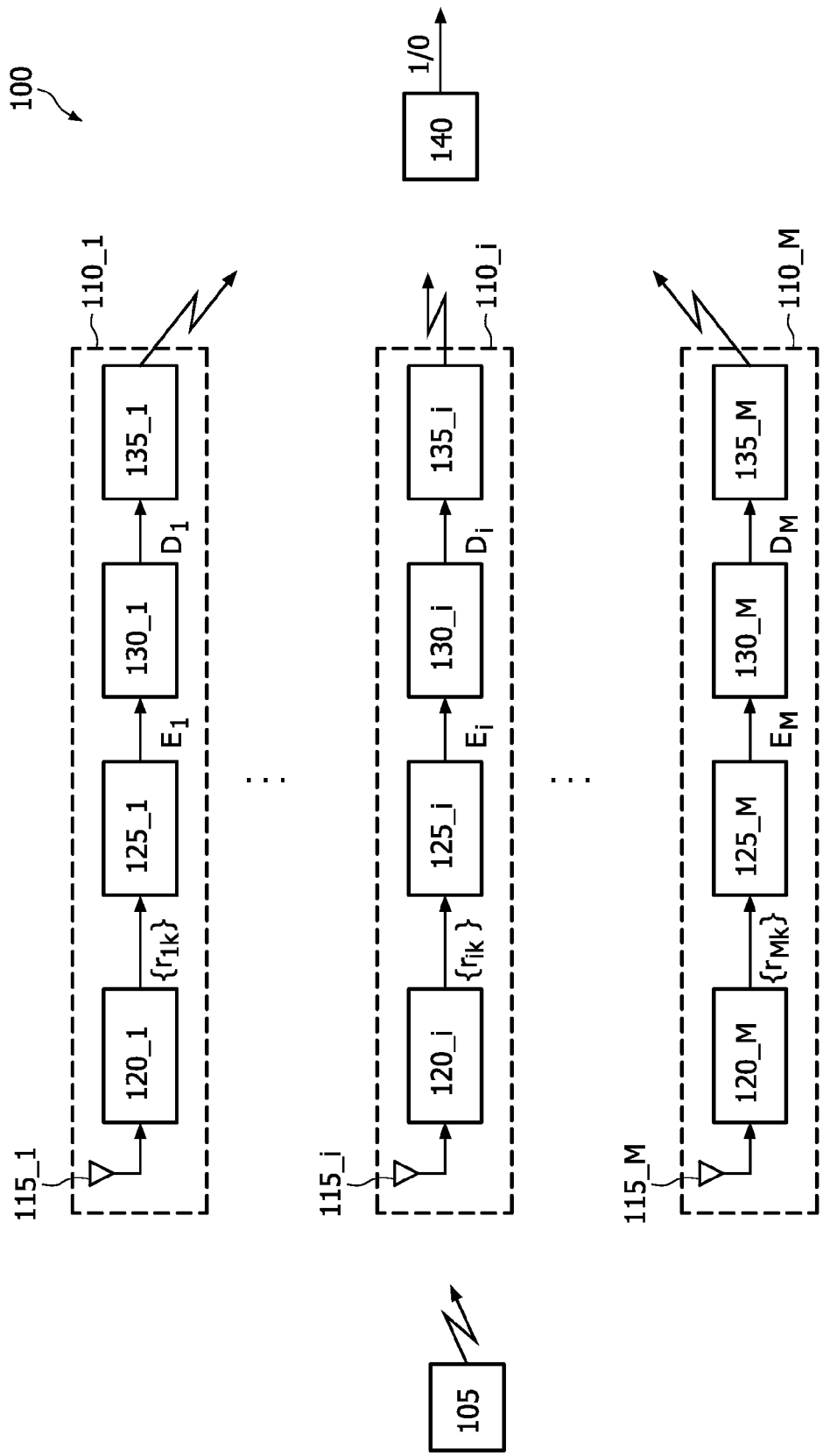
FIG. 1 shows a schematic block diagram illustrating the arrangement of an exemplary system according to a first embodiment.

FIG. 1 shows a schematic block diagram illustrating the arrangement of an exemplary system 100 according to the first embodiment. The system 100 can comprise a transmitter 105, first to M-th devices 110_1 to 110_M distributed over a region, and a central unit 140. Each of the devices 110_1 to 110_M may include an antenna, a sensing unit, a first computing unit, a second computing unit and a communicating unit. That is, an i-th device 110_i can comprise an antenna 115_i, a sensing receiver or unit 120_i, a first computing unit 125_i, a second computing unit (130_i) and a communicating unit 135_i. For example, the first device 110_1 may include an antenna 115_1, a sensing unit 120_1, a first computing unit 125_1, a second computing unit (130_1) and a communicating unit 135_1, and the M-th device 110_M can comprise an antenna 115_M, a sensing unit 120_M, a first computing unit 125_M, a second computing unit (130_M) and a communicating unit 135_M.

A device 110_i can have a structure different from that discussed above. For example, it can comprise just a single computing unit having the functionality of both the first computing unit 125_i and the second computing unit 130_i, or some kind of processing unit capable of performing the functions of all components of the device 110_i. In general, each of the devices 110_1 to 110_M may be a sensing receiver with communication capabilities to a central unit, such as e.g. a sensing radio, or another kind of device capable of performing the functions described below.

The system 100 can be part of a secondary cognitive wireless system. Such secondary cognitive wireless system enables a secondary usage of a spectrum that has been licensed for a primary wireless system, without causing a harmful interference to primary system users. This may be achieved by operating on portions of the spectrum that are not used for primary user transmissions. To determine these portions, primary user signals can be detected by spectrum sensing. That is, it may be determined whether or not a signal of interest is present in a certain frequency band.

The problem of primary user signal detection can be considered as a binary hypothesis testing problem—determining which of two hypotheses, signal of interest present (hypothesis denoted by $H_1$) or only noise present (hypothesis denoted by $H_0$), is true. The signal presence may be detected by the M devices 110_1 to 110_M of the system 100 as described in further detail below.

A signal of interest can be transmitted by the transmitter 105 and may be e.g. a radio frequency (RF) signal such as a signal in the VHF band or the UHF band. For example, a microwave signal can be transmitted. Each of the devices 110_1 to 110_M may receive or sense the signal transmitted by the transmitter 105. That is, each of the sensing units 120_1 to 120_M can respectively receive or sense the transmitted signal received at the corresponding one of the antennas 115_1 to 115_M. Further, each of the sensing units 120_1 to 120_M may sample the sensed signal. This can be done by sampling the analog signal after the respective front-end receive antenna of the antennas 115_1 to 115_M. Then, samples of the sensed signal may be collected over an observation time. This can be achieved by sampling the sensed signal at the sensing units 120_1 to 120_M at the Nyquist frequency or a higher frequency. That is, oversampling is possible. The collected samples of the received or sensed signal are denoted $r_{ik}$, wherein the subscript i denotes the i-th sensing unit 120_i and the subscript k denotes a sample index.

The sampled sensed signal at the i-th sensing unit 120_i under the two hypotheses $H_1$ and $H_0$, respectively, may then be written as:

$$H_1: r_{ik} = s_{ik} + n_{ik},$$

$$H_0: r_{ik} = n_{ik} \tag{1}$$

wherein $s_{ik}$ denotes a k-th signal sample at the i-th sensing unit 120_i and $n_{ik}$ denotes a k-th independent Gaussian noise sample at the i-th sensing unit 120_i.

The signal samples $r_{ik}$ can be supplied from the i-th sensing unit 120_i to the i-th first computing unit 125_i and then be used to compute a quantity or value $E_i$ according to e.g. the following equation:

$$E_i = \frac{1}{2N_0 W} \sum_{k=1}^{2\Lambda} r_{ik}^2, \tag{2}$$

wherein $\Lambda$ denotes the time-bandwidth product, $N_0$ denotes the noise power and W denotes the signal bandwidth. The computation of the value $E_i$ according to the equation (2) may be performed by using e.g. a square-and-sum unit of the i-th first computing unit 125_i.

$E_i$ denotes a random variable and has a different distribution function depending on the hypothesis. Under the hypothesis $H_0$, $E_i$ can have a central chi-squared distribution with $2\Lambda$ degrees of freedom. Under the hypothesis $H_1$, $E_i$ may have a non-central chi-squared distribution with $2\Lambda$ degrees of freedom and a non-centrality parameter $2\rho_i$, wherein $\rho_i$ is the signal-to-noise ratio (SNR). That is, given $H_0$ the probability distribution of $E_i$ can be a central chi-squared distribution, while given $H_1$ the probability distribution of $E_i$ may be a non-central chi-squared distribution.

Based on the value $E_i$ computed according to the above equation (2), the i-th second computing unit 130_i can compute e.g. the following quantity or soft metric:

$$D_i = \log\left(\frac{P(E_i | H_1)}{P(E_i | H_0)}\right), \tag{3}$$

wherein $P(E_i|H_0)$ and $P(E_i|H_1)$ are the respective probabilities of $E_i$ given $H_0$ and $H_1$. That is, $P(E_i|H_0)$ denotes a conditional probability under the condition that the hypothesis $H_0$ is true, and $P(E_i|H_1)$ denotes a conditional probability under the condition that the hypothesis $H_1$ is true.

$P(E_i|H_0)$ and $P(E_i|H_1)$ may be computed based on the probability distribution functions of $E_i$ under the hypotheses $H_0$ and $H_1$, respectively. Then, the metric $D_i$ can be computed according to the above equation (3). However, alternative metrics may be computed according to other equations. For example, the metric $D_i$ can be computed based on the likelihood ratio instead of the log-likelihood ratio. In this case, the metric $D_i$ may be computed e.g. according to the following equation:

$$D_i = \log\left(\frac{P(E_i | H_1)}{P(E_i | H_0)}\right) \tag{3'}$$

Further, not only likelihood ratios but also other functions that suitably depend on $P(E_i|H_0)$ and $P(E_i|H_1)$ may be utilized in the computation. It is also possible to use suitably quantized versions of such functions.

The computation of the metric $D_i$ according to the above equation (3) can involve a division function and a log function. These functions may be implemented by using standard functional blocks capable of computing them. Such blocks can be part of the second computing unit 130_i. In case the metric $D_i$ is computed in a different manner, other functions may be involved. For example, when using the likelihood ratio instead of the log-likelihood ratio, only a division function can be involved. Thus, in this case a simple divider may be sufficient.

The metric $D_i$ computed by the second computing unit 130_i can be supplied to the communicating unit 135_i. The communicating unit 135_i may then communicate the metric $D_i$ to the central unit 140. That is, this metric may be signaled from the device 110_i to the central unit 140. The devices 110_1 to 110_M can communicate with the central unit 140 under a defined protocol. The information element to be communicated may be specified. For example, it can be the soft information or metric $D_i$ as computed according to the equation (3) or the equation (3'). The communication can be a wireless or wired communication.

Communicated information from the devices 110_1 to 110_M, i.e. the metrics $D_1$ to $D_M$, may be received and collected at the central unit 140. Then, the communicated information can be combined. For example, the metrics $D_1$ to $D_M$ may be summed. Based on the combined information, a final detection of the signal of interest can be performed. In other words, the central unit 140 can determine whether the hypothesis $H_1$ is true, i.e. the signal of interest is present, or the hypothesis $H_0$ is true, i.e. only noise is present. For example, the following decision rule may be used to declare either $H_1$ or $H_0$ true:

$$D_s(\vec{E}_M) = \sum_{i=1}^{M} D_i \tag{4}$$

$$= \sum_{i=1}^{M} \log\left(\frac{P(E_i | H_1)}{P(E_i | H_0)}\right) \begin{cases} \geq \zeta & \text{declare } H_1 \text{ true} \\ < \zeta & \text{declare } H_0 \text{ true} \end{cases}$$

According to the above equation (4), a final decision statistic $D_s$, depending on a vector $\vec{E}_M$ can be determined as a sum of the metrics $D_1$ to $D_M$ from the M devices 110_1 to 110_M. The components of the vector $\vec{E}_M$ may be values computed according to the above equation (2). That is, the vector $\vec{E}_M$ can comprise a set of values $E_1$ to $E_M$ computed by the M first computing units 125_1 to 125_M. Thus, the following relation may apply:

$$\vec{E}_M = \begin{pmatrix} E_1 \\ E_2 \\ \vdots \\ E_M \end{pmatrix} \tag{5}$$

In the above equation (4), the vector $\vec{E}_M$ is explicitly written to indicate that the final decision statistic $D_s$, can be a function of the values $E_1$ to $E_M$. After determining $D_s$, this final decision statistic may be compared with a detection threshold $\zeta$. If $D_s$ is greater than or equal to $\zeta$, the hypothesis $H_1$ can be declared true. If $D_s$ is less than $\zeta$, the hypothesis $H_0$ may be declared true. The detection threshold $\zeta$ can be chosen to optimize the detection performance of the system 100. It may be computed a priori and can also be adapted while the system 100 is operating.

According to the equation (4) the final decision statistic $D_s$, can be computed as a sum of the $D_i$'s and then compared with the detection threshold $\zeta$. These operations may be effected by e.g. a summing and comparing unit. The output of such unit can be 1 if a resulting value of $D_s$ is greater than or equal to the detection threshold $\zeta$ and may otherwise be 0. The output can also be 0 for a value of $D_s$ that is greater than or equal to the detection threshold $\zeta$ and may otherwise be 1. Further, outputs other than 1 and 0 can be associated with different values of $D_s$.

As described above, the final decision statistic $D_s$ may be determined by summing $D_1$ to $D_M$ if the metric $D_i$ is computed based on the log-likelihood ratio, i.e. according to the equation (3). The determination can be performed in a different manner in case the metric $D_i$ is computed based on another suitable function. The kind of determination may be selected in dependence on the kind of computation of the metric $D_i$. For example, if the likelihood ratio instead of the log-likelihood ratio is utilized, i.e. the metric $D_i$ is computed according to the equation (3'), the final decision statistic $D_s$ can be determined by multiplying $D_1$ to $D_M$. In this case e.g. the following decision rule may be used to declare either $H_1$ or $H_0$ true:

$$D_s\left(\vec{E}_M\right) = \prod_{i=1}^{M} D_i \qquad (4')$$

$$= \prod_{i=1}^{M} \frac{P(E_i \mid H_1)}{P(E_i \mid H_0)} \begin{cases} \geq \zeta & \text{declare } H_1 \text{ true} \\ < \zeta & \text{declare } H_0 \text{ true} \end{cases}$$

As a result of the above-described detection procedure, the central unit 140 can determine a value indicating whether the hypothesis $H_0$ or the hypothesis $H_1$ has been declared true. For example, the central unit 140 may determine a value 0 if $H_0$ has been declared true and a value 1 if $H_1$ has been declared true, or vice versa. Other values can also be associated with the hypotheses $H_0$ and $H_1$. The central unit 140 may output the determined value.

Based on a result of the performed detection procedure, e.g. a value determined by the central unit 140, an apparatus such as e.g. a radio apparatus that wants to perform a secondary user transmission can be allowed to access a certain frequency band if no primary user transmission is taking place in this frequency band. Otherwise, the apparatus may not be allowed to access the certain frequency band. That is, a radio access can be controlled based on the result of the detection procedure. Such control may be performed by the central unit 140 or an additional control unit not shown in FIG. 1. In the latter case, the additional control unit can perform the control e.g. based on a value determined and output by the central unit 140.

According to the above description, samples $r_{ik}$ of the sensed signal may be collected. That is, the i-th first computing unit 125_i can compute the value $E_i$ based on multiple samples of the sensed signal. However, it is also possible that samples of a signal component derived from the sensed signal are collected and the value $E_i$ is computed based on these samples. For example, samples of a pilot component embedded in the sensed signal may be collected and used to compute the value $E_i$. The signal component can be extracted from the sensed signal in the i-th first computing unit 125_i. It may also be extracted in a separate unit providing the signal component to the i-th first computing unit 125_i, even if no such separate unit is shown in FIG. 1.

Further, a detection procedure for detecting a signal of interest is described above in the context of an exemplary arrangement where a single primary signal such as e.g. a radio signal is transmitted by a single transmitter such as the transmitter 105 shown in FIG. 1. However, the detection procedure can also be applied to arrangements where a plurality of primary signals is transmitted by one or more transmitters, i.e., when an aggregation of multiple signals occurs. That is, even if this is not shown in FIG. 1, a plurality of transmitters may be present.

Figure 2:
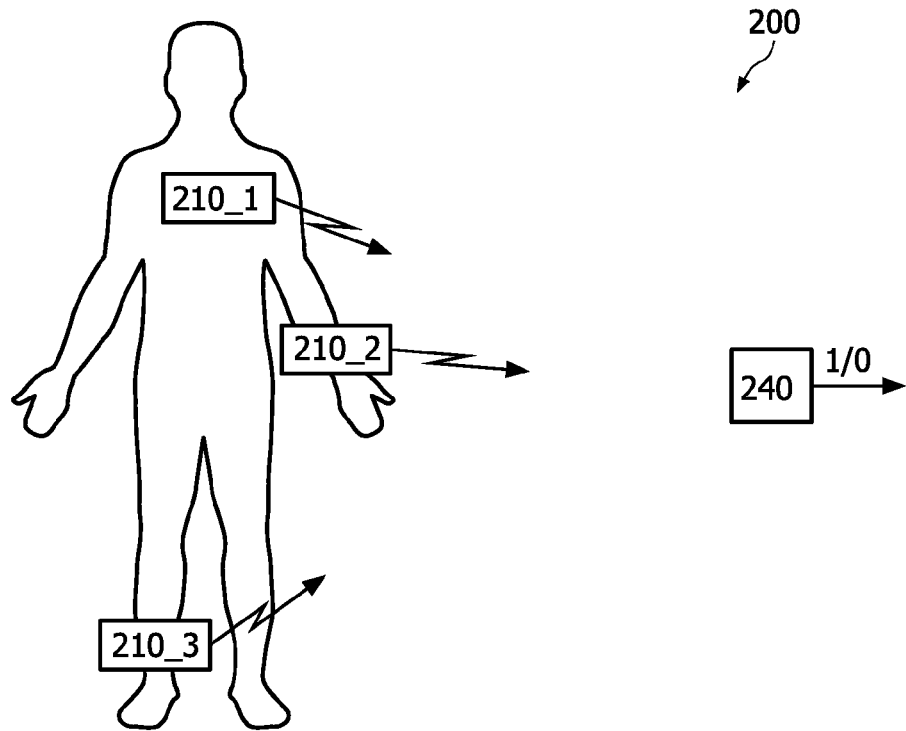
FIG. 2 shows a schematic block diagram illustrating the arrangement of an exemplary system according to a second embodiment.

FIG. 2 shows a schematic block diagram illustrating the arrangement of an exemplary system 200 according to the second embodiment. The system 200 can comprise a plurality of devices, e.g. first to third devices 210_1 to 210_3, and a central unit 240. The devices 210_1 to 210_3 may be part of a sensor network distributed over a human body as depicted in FIG. 2, or another kind of network. Each of the devices 210_1 to 210_3 may include components similar to those of the devices 110_1 to 110_M in the system 100 according to the first embodiment. That is, each device can comprise an antenna or coupling unit, a sensing unit, a first computing unit, a second computing unit and a communicating unit.

The second embodiment differs from the first embodiment in that it involves a detection of events rather than radio signals. For example, some physiological parameter such as e.g. heart rate, brain electrical activity or muscular activity may be detected. Such parameter can be detected by a sensor network comprising a set of sensitive sensors capable of measuring the desired quantity. For example, a sensor network including sensors capable of sensing physiological signals such as e.g. electrocardiogram (ECG) signals, electroencephalogram (EEG) signals and/or electromyogram (EMG) signals may be used.

Devices or sensors of a sensor network according to the second embodiment can for instance be distributed over a human or animal body. The hypothesis $H_1$ in this case may represent a presence (an occurrence), or a deviation from a normal value, of a physiological source or parameter. On the other hand, the hypothesis $H_0$ can represent its absence, or being at the normal state. For example, $H_0$ and $H_1$ may represent a normal heartbeat and a heart arrhythmia of a person.

The steps described in connection with the first embodiment remain similar with the appropriate changes in nomenclature, with the difference that the underlying probability distributions under the hypotheses $H_0$ and $H_1$ can now be different depending on the statistical nature of the event to be detected.

Figure 3:
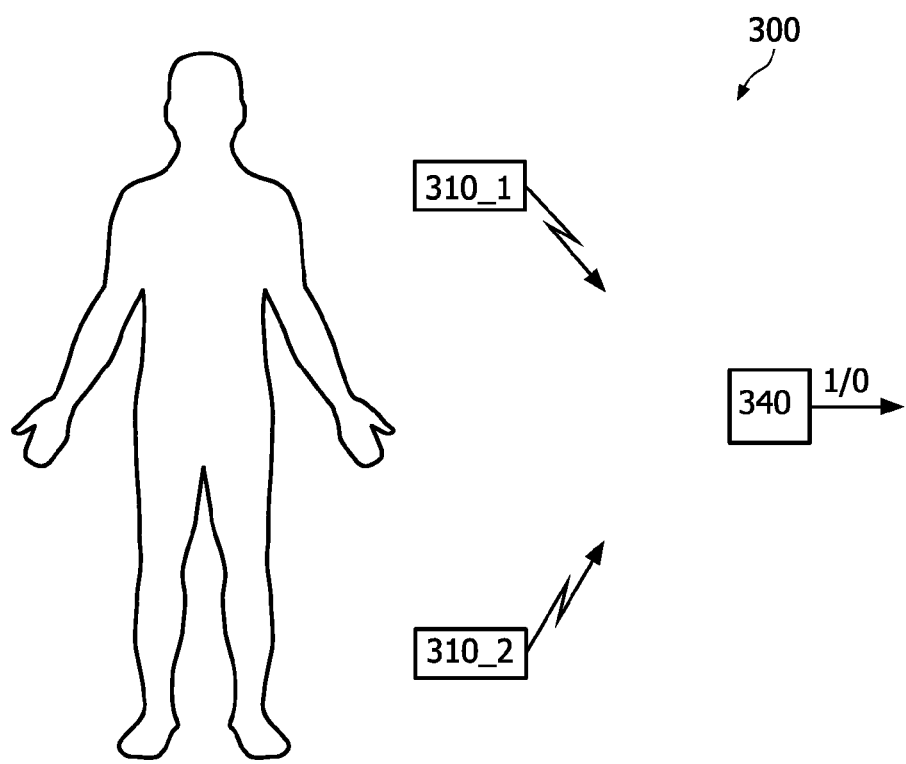
FIG. 3 shows a schematic block diagram illustrating the arrangement of an exemplary system according to a third embodiment.

FIG. 3 shows a schematic block diagram illustrating the arrangement of an exemplary system 300 according to the third embodiment. The system 300 can comprise a plurality of devices, e.g. first and second devices 310_1 and 310_2, and a central unit 340. The devices 310_1 and 310_2 may be part of a sensor network distributed in an environment of a human or animal body such as e.g. a surrounding home environment. For example, the devices 310_1 and 310_2 can be located next to a human body as depicted in FIG. 3. Each of the devices 310_1 and 310_2 may include components similar to those of the devices 110_1 to 110_M in the system 100 according to the first embodiment. That is, each device can comprise an antenna or coupling unit, a sensing unit, a first computing unit, a second computing unit and a communicating unit.

The third embodiment is similar to the second embodiment. With this embodiment a presence or absence of a human being or an animal rather than that of a physiological source or parameter may be detected. More specifically, it can be detected whether or not a human or animal body is present in a certain area. In this case e.g. the hypothesis $H_1$ may represent a presence of a person, and the hypothesis $H_0$ can represent its absence.

The steps described in connection with the first embodiment remain similar with the appropriate changes in nomenclature, with the difference that the underlying probability distributions under the hypotheses $H_0$ and $H_1$ may now be different depending on the detection target.

Figure 4:
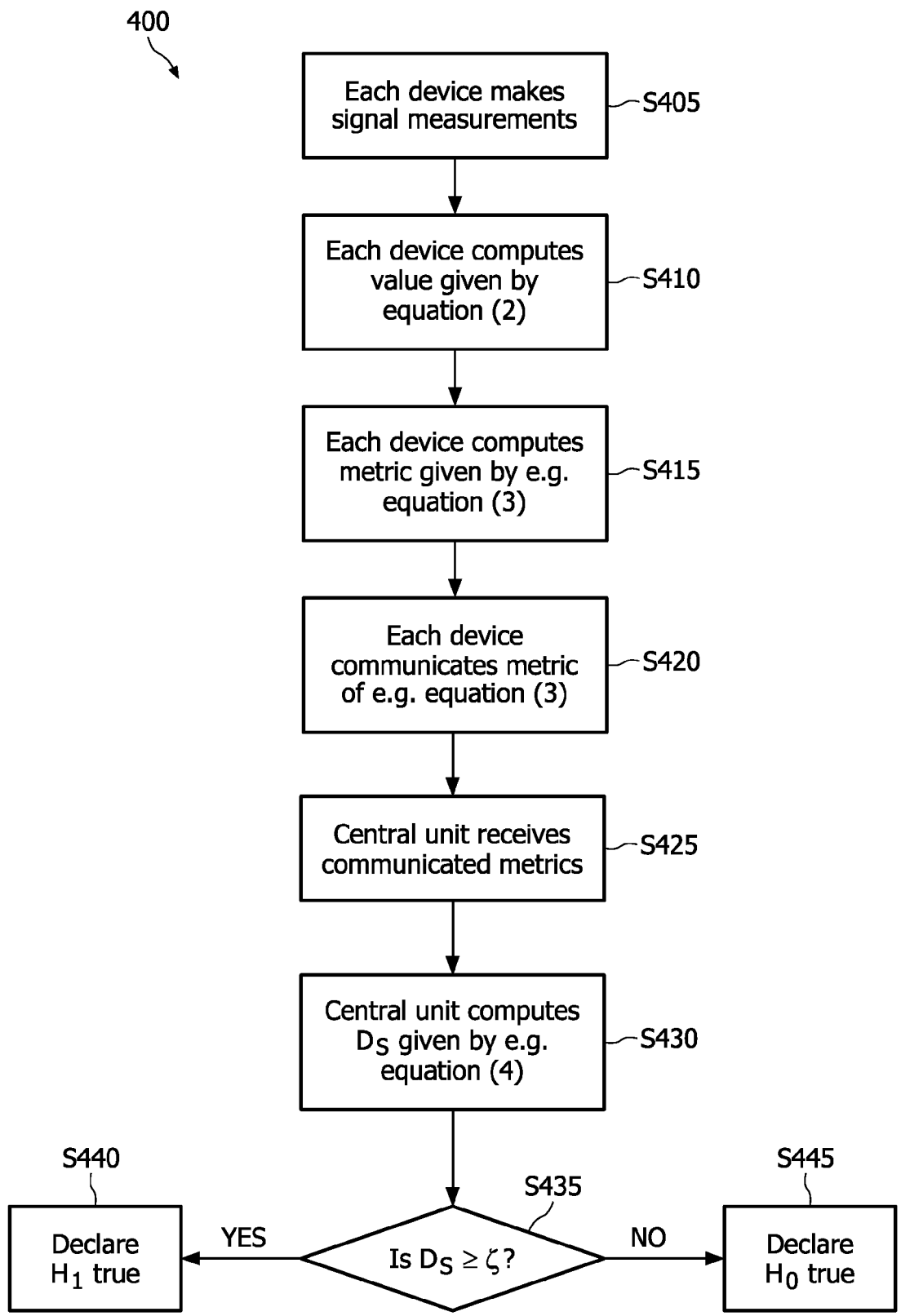
FIG. 4 shows a flowchart illustrating steps of an exemplary detection procedure according to the first to third embodiments.

FIG. 4 shows a flowchart illustrating steps of an exemplary detection procedure 400 according to the first to third embodiments. The depicted steps can be executed by the devices 110_1 to 110_M and the central unit 140 of the system 100 shown in FIG. 1 when performing the above described detection procedure in accordance with the first embodiment. They can also be executed by corresponding elements of the system 200 when performing a detection procedure according to the second embodiment, or by corresponding elements of the system 300 when performing a detection procedure according to the third embodiment.

In a step S405 of the detection procedure 400, each device can make signal measurements. That is, each device may sense a signal and sample the same. For example, a transmitted signal or a physiological signal can be sensed. In a step S410, each device may compute a value given by the equation (2). In a step S415, each device can compute a metric given by e.g. the equation (3). In a step S420, each device may communicate the respective computed metric. In a step S425, the central unit can receive the communicated metrics from the devices. In a step S430, the central unit may compute the final decision statistic $D_s$, given by e.g. the equation (4). In a step S435, it can be determined whether or not $D_s$ is greater than or equal to the detection threshold $\zeta$. If the determination in step S435 is positive ("Yes"), the hypothesis $H_1$ may be declared true in a step S440. In case the determination in step S435 is negative ("No"), the hypothesis $H_0$ may be declared true in a step S445.

Figure 5:
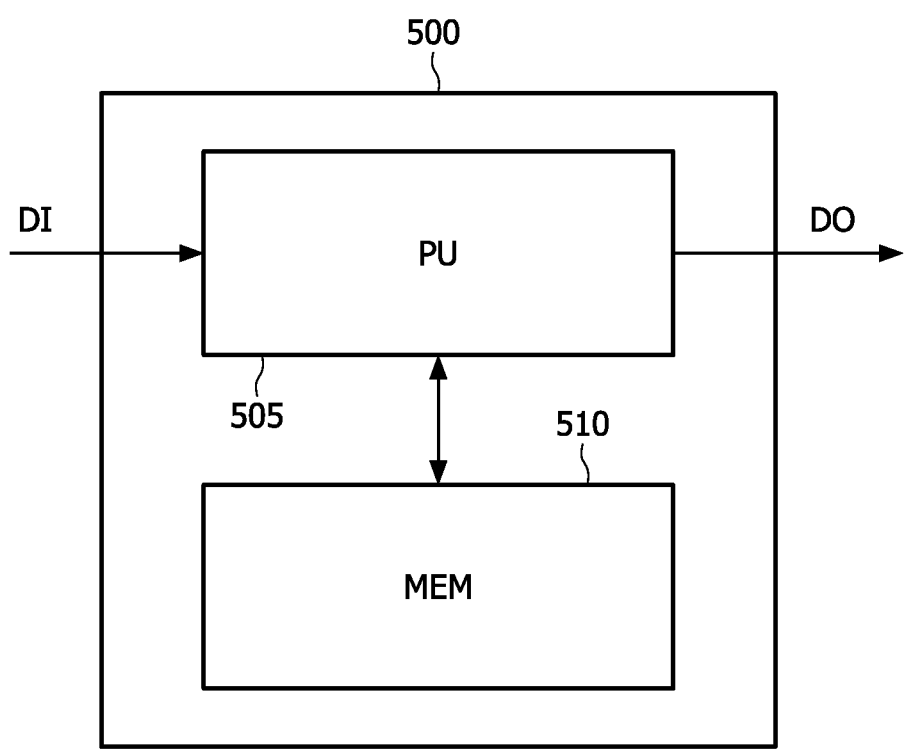
FIG. 5 shows an example of a software-based implementation of the first to third embodiments.

FIG. 5 shows an example of a software-based implementation of the first to third embodiments. Here, a device 500 comprises a processing unit (PU) 505, which may be provided on a single chip or a chip module and which may be any processor or computer entity with a control unit that performs control based on software routines of a control program stored in a memory (MEM) 510. Program code instructions are fetched from the MEM 510 and loaded into the control unit of the PU 505 in order to perform processing steps such as described in connection with FIG. 4 or defined in the claims. The processing steps depicted in the flowchart of FIG. 4 or similar processing steps can be performed on the basis of input data DI and may generate output data DO. The input data DI can correspond to signals that have been sensed, and the output data DO may correspond to a decision result indicating which one of a plurality of hypotheses is true.

The advantages of the proposed detection procedure become obvious when comparing its detection performance with that of a detection procedure using a hard detection in a system comprising 5 devices respectively having a single sensing unit. A clear performance gain can be seen. Such performance gain may also be seen in comparison with a system comprising just one device having a single sensing unit.

The detection performance of a system can be measured in terms of the achieved probability of false alarm ($P_{fa}$), for a set probability of missed detection ($P_{md}$). For example, $P_{md}=10^{-3}$ may be set.

Figure 6:
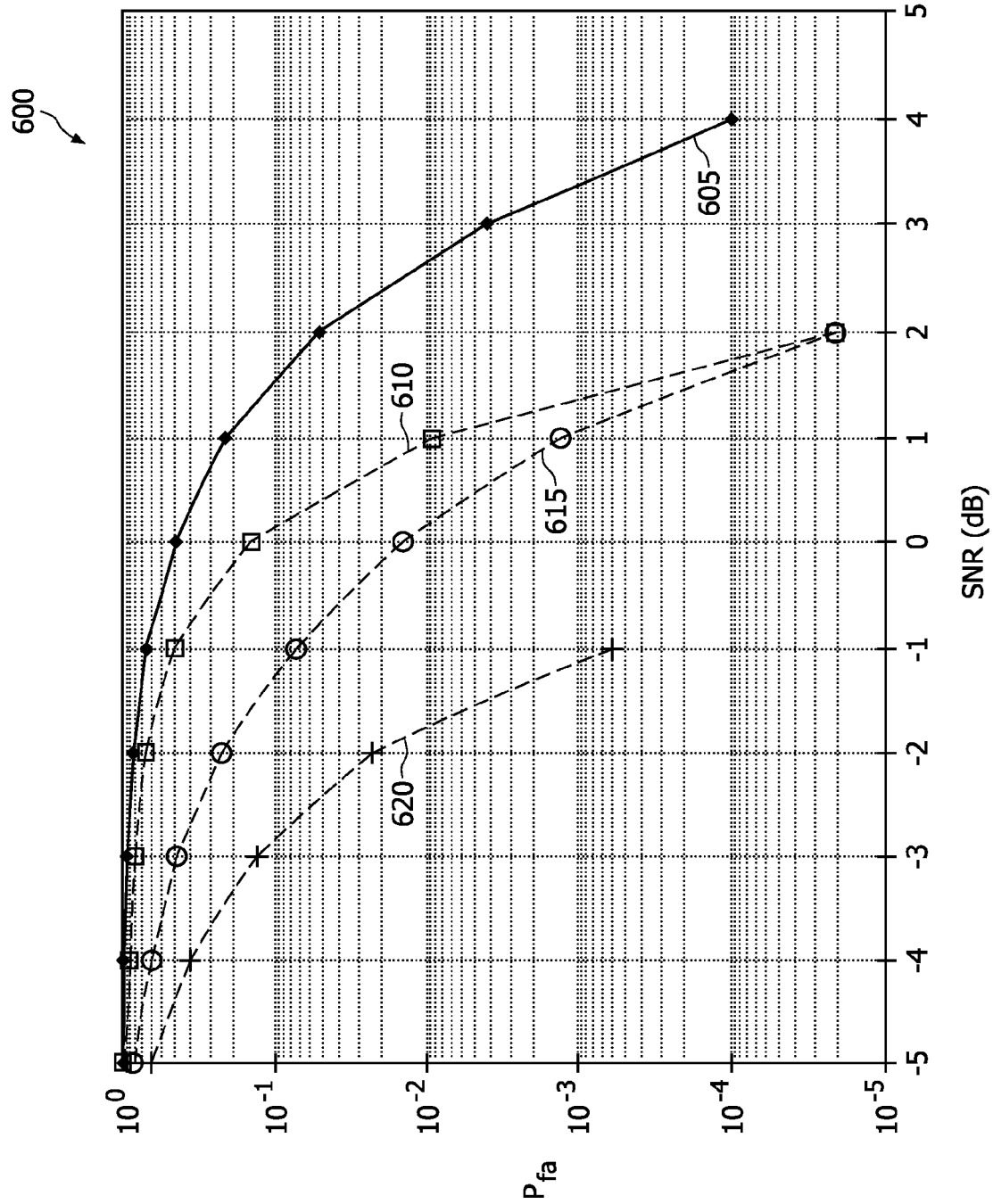
FIG. 6 shows a graph illustrating the performance of an exemplary detection procedure according to the first to third embodiments in comparison with the performances of previously proposed detection procedures.

FIG. 6 shows a graph 600 illustrating the performance of an exemplary detection procedure according to the first to third embodiments in comparison with the performances of previously proposed detection procedures. The depicted graph 600 shows the achieved $P_{fa}$ of the different approaches in dependence on the signal-to-noise ratio (SNR), when $P_{md}$ is set to $10^{-3}$. A curve 605 illustrates the $P_{fa}$ of a previously proposed detection procedure using a hard detection in a system comprising only one device having a single sensing unit or sensor. A curve 610 illustrates the $P_{fa}$ of a previously proposed detection procedure using a hard detection in a system comprising 5 devices respectively having a single sensing unit or sensor, wherein an AND combination is applied to values output by these devices. A curve 615 illustrates the $P_{fa}$ of a previously proposed detection procedure using a hard detection in a system comprising 5 devices respectively having a single sensing unit or sensor, wherein an OR combination is applied to values output by these devices. A curve 620 illustrates the $P_{fa}$ of an exemplary detection procedure according to the first to third embodiments in a system comprising 5 devices respectively having a single sensing unit or sensor. The depicted curves illustrate supporting simulation results.

It is clear from the graph 600 that the probability of false alarm $P_{fa}$ can be considerably lower with the detection procedure according to the first to third embodiments than with the previously proposed detection procedures. This means that a system such as e.g. a cognitive wireless system using the detection procedure according to the first to third embodiments may have more opportunities to access empty spectrum, since the probability that it falsely declares that empty spectrum is occupied is low. Thus, its performance can be better.

The detection procedure according to the first to third embodiments may be applied to enhancements that are likely to happen once the upcoming IEEE 802.22 standard on Wireless Regional Area Networks (WRANs) is completed. Future standardization is expected to be targeted towards connectivity applications (e.g. portable devices) in the UHF bands/TV white space where the proposed detection procedure would be of great interest. The proposed detection procedure can be more generally applied to a wide class of cognitive wireless systems and other systems that may be subject to future standardization.

A variety of applications utilizing the presented solution for signaling and combining soft information for distributed spectrum sensing can be contemplated, in particular as future wireless systems are expected to be cognitive in nature. The proposed detection procedure may in general be applied to understand the signal environment—detecting types of signals of interest and interference present in a certain spectrum of interest. It can also be used for applications like e.g. an event detection by a diverse sensor network.

In the present application a detection procedure for cognitive wireless systems comprising multiple devices or sensors with communication capabilities to a central unit is proposed. This detection procedure can be used e.g. in a spectrum sensing method for detecting certain signals of interest by a cognitive wireless network. Rules and signaling protocols may be used to determine whether or not a signal of interest is present in a certain frequency band or to detect a certain event. The proposed detection procedure can be utilized with multiple devices distributed over a region. Each of the devices may perform signal detection or sensing, collect received signal samples over an observation time, compute a soft detection metric (e.g. a likelihood ratio, a log-likelihood ratio or another suitable function) and transmit/signal the soft detection metric to a central unit. The metric can be an energy metric and may be conditioned on different hypotheses. The soft detection metrics from the multiple devices can be collected at the central unit. The central unit may combine the collected metrics by means of a specified fusion or combination rule and then use a threshold rule in order to make a final decision on the presence or absence of the signal of interest or event, e.g. to detect a primary user signal.

The proposed detection procedure can provide a better detection performance in comparison with previously proposed approaches, without requiring much more signaling overhead. This may be rendered possible by the feedback metric and the fusion rule used by the detection procedure. The former can take the form of a signaling protocol, and would be useful in any standard in cognitive radios, or future standards in sensor networks.

In summary, the invention relates to a device, a system, a method and a computer program for spectrum sensing. A detection procedure for detecting a signal of interest or an event by using a plurality of sensing devices capable of communicating with a central unit is proposed. The sensing devices can compute soft detection metrics and communicate this information to a central unit, where the information may be used to make a final detection decision using a certain specified rule. The signaling overhead of the proposed approach can be of the same order as that of a hard signaling approach. However, the proposed approach may achieve a better detection performance.

While the present invention has been illustrated and described in detail in the drawings and foregoing description, such illustration and description are to be considered illustrative or exemplary and not restrictive. The invention is not limited to the disclosed embodiments.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor, computing unit, sensing unit or other unit may fulfill the functions of several items recited in the claims. The mere fact that certain measures are recited in mutually different dependent claims does not indicate that a combination of these measures cannot be used to advantage.

A computer program capable of controlling a processor to perform the claimed features can be stored/distributed on a suitable medium, such as an optical storage medium or a solid-state medium supplied together with or as part of other hardware, but may also be distributed in other forms, such as via the Internet or other wired or wireless telecommunication systems. A computer program product for a computer can comprise software code portions for performing e.g. processing steps such as those described in connection with FIG. 4 when the computer program product is run on the computer. The computer program product may further comprise a computer-readable medium on which the software code portions are stored, such as e.g. an optical storage medium or a solid-state medium.

Any reference signs in the claims should not be construed as limiting the scope thereof.

The invention claimed is:

1. A plurality of similar devices to determine secondary usage portions of a wireless spectrum licensed for but not used for primary usage transmissions, each device comprising:
    an antenna;
    a sensor coupled to the antenna and configured to sense one or more transmissions of primary usage from at least one wireless transmitter and to collect one or more samples of the one or more sensed transmissions;
    one or more processors configured to compute a value based on said one or more sensed transmissions, and configured to compute a metric, which is a function based on conditional probabilities of a relationship of said computed value to a plurality of hypotheses; and
    a communicating unit configured to communicate said metric to a controller, and to receive a determination from the controller indicating if the computed value represents the primary usage or noise, and
    determining the secondary usage portions of the wireless spectrum based on the indication.

2. The device according to claim 1, wherein said value is computed based on a sum of squared samples of said one or more sensed transmissions or one or more sensed transmission components.

3. The device according to claim 1, wherein said metric is computed based on conditional probabilities of said value.

4. The device according to claim 1, wherein said metric is one of a loci-likelihood ratio and likelihood ratio.

5. The device according to claim 1, wherein said sensor is configured to collect samples of said one or more sensed transmissions over an observation time.

6. The device according to claim 1, wherein said one or more transmissions are at least one of a radio signal or physiological signal.

7. A system to determine secondary usage portions of a wireless spectrum licensed for but not used for primary usage transmissions, the system comprising:
    at least one wireless transmitter for continuously transmitting one or more transmissions;
    a plurality of devices distributed over a region, each device including
        an antenna,
        a sensor coupled to the antenna and configured to sense one or more transmissions of primary usage from the at least one wireless transmitter and to collect one or more samples of the one or more transmissions,
        one or more processors configured to compute a value based on said one or more sensed transmissions, and a metric which is a function based on conditional probabilities of a relationship of said computed value to a plurality of hypotheses, and
        a communicating unit configured to communicate said metric; and
    a controller configured to receive the metrics communicated by said devices, to combine said metrics, and to decide based on said combined metrics which one of the plurality of hypotheses is true, and
    determining the secondary usage portions based on the decision.

8. The system according to claim 7, wherein said metrics are combined by summing or multiplying.

9. The system according to claim 7, wherein said decision is made using a threshold rule.

10. The system according to claim 7, wherein said plurality of devices are part of a cognitive wireless network or sensor network.

11. The system according to claim 7, wherein said controller is configured to determine the transmissions of primary usage in a frequency band of the wireless spectrum or to detect a certain event.

12. A method for utilizing a plurality of devices to determine secondary usage portions of a wireless spectrum licensed for but not used for primary usage transmissions, the method comprising acts of:
    on each of the plurality of devices:
        sensing one or more transmissions of primary usage from at least one wireless transmitter,
        collecting one or more samples of the one or more sensed transmissions,
        computing a value based on one or more said sensed transmissions, and a metric, which is a function based on conditional probabilities of a relationship of said computed value to a plurality of hypotheses
        communicating said metric to a controller; and
    on the controller
        combining the metrics, and
        determining based on the combined metrics which one of the plurality of hypotheses is true and if the computed value represents the primary usage or noise, and
    determining the secondary usage portions depending on if the computer values represents the primary usage or noise.

13. The method according to claim 12, wherein the method is encoded as program code for causing a computer to carry out the acts of the method when said computer program is carried out on a computer.

* * * * *